United States Patent
Robbins, Jr.

(10) Patent No.: US 6,841,384 B2
(45) Date of Patent: Jan. 11, 2005

(54) ADVANCED ROLLER BOTTLE SYSTEM FOR CELL AND TISSUE CULTURING

(75) Inventor: Neil F. Robbins, Jr., Cary, NC (US)

(73) Assignee: Becton Dickinson Company, Franklin Lakes, NJ (US)

( * ) Notice: Subject to any disclaimer, the term of this patent is extended or adjusted under 35 U.S.C. 154(b) by 349 days.

(21) Appl. No.: 10/214,324

(22) Filed: Aug. 8, 2002

(65) Prior Publication Data

US 2004/0029264 A1 Feb. 12, 2004

(51) Int. Cl.⁷ .................................................. C12N 5/00
(52) U.S. Cl. ................ 435/325; 435/286.5; 435/288.1; 435/298.1; 435/298.2; 435/304.1; 435/395
(58) Field of Search ............................... 435/325, 286.5, 435/288.1, 298.1, 298.2, 304.1, 395

(56) References Cited

U.S. PATENT DOCUMENTS

| 4,912,058 A | 3/1990 | Mussi et al. ................. 435/285 |
| 6,323,022 B1 | 11/2001 | Chang et al. ............. 435/286.5 |

*Primary Examiner*—Leon B. Lankford, Jr.

(57) ABSTRACT

The invention provides an advanced roller bottle system for cell culture that efficiently, continually, and automatically replenishes spent media with fresh media. The roller bottle system optimizes media use by removing spent media in response to a predetermined condition change and replenishing the spent media with fresh.

26 Claims, 3 Drawing Sheets

ADVANCED ROLLER BOTTLE SYSTEM FOR CELL AND TISSUE CULTURING

BACKGROUND OF THE INVENTION

1. Field of the Invention

The present invention is generally related to the culturing of cells and more particularly to a multi-chambered roller bottle suitable for the preparation of cellular products.

2. Description of the Background Art

Roller bottles are routinely used for the growth of cells and the production of cellular products. Cultivation of cells occurs after the roller bottle is placed within a rotating apparatus, e.g., RollerCell 40™ from Synthecon, Inc. or the $R_2P$ Roller Culture Apparatus™ from Zinsser Analytic, Ltd. (UK).

There is a continuing need to enhance cell culture efficiency and product yields. Generally, culture or product production conditions are empirically optimized for a cell type. Other approaches exist for determining operating parameters. Then a feedback control mechanism is typically used to insure that conditions are maintained within these optimized parameters. Some of the feedback control systems can be complex or not readily adaptable to roller bottle culture systems. For example, see U.S. Pat. Nos. 4,839,292 and 6,323,022.

SUMMARY OF THE INVENTION

The invention provides an advanced roller bottle system (ARBS) for cell culture that efficiently, continually, and automatically replenishes spent media with fresh media. ARBS optimizes media use by removing spent media in response to a predetermined condition change and replenishing the spent media with fresh.

The ARBS system includes a multi-chambered bottle where the chambers are cylindrical and are in controlled fluid communication with each other. In one embodiment, a first cylindrical chamber is a reservoir for fresh media; a second cylindrical chamber is a cell or tissue growth chamber and a third cylindrical chamber is a reservoir for holding spent media. Fluid communication between the chambers is by way of transfer chambers and control is achieved by valve operation. The fluid communication between the first and second chambers allows controlled addition of new media once an operational parameter is met. The fluid communication between the second and third chamber allows the withdrawal of media from the second once its spent or a threshold concentration of cellular product is attained.

The fluid communication is regulated or controlled by a set of control valves situated in ports between the cylindrical chambers. The opening and closing of the control valves allows media to flow from one cylindrical chamber to the next via the transfer chamber. The fresh media transfer chamber can be situated between the first and second cylindrical chambers or include portions of one or more of these chambers. Like wise, the spent media chamber can be situated between the second and third cylindrical chambers or involve portions of one or more of these chambers.

In one embodiment, the roller bottle rotates clockwise or counter clockwise about its axis of rotation causing media to be transferred from one chamber to the next by gravity.

The fresh media transfer chamber scoops and holds a predetermined volume of fresh media from the first cylindrical chamber as the ARBS rotates. The held media is released to the second chamber upon actuation of a valve. At the six o'clock position, the control valve that permits the flow of media from the second cylindrical chamber to the spent media transfer chamber is opened by a solenoid activated by a gravity sensitive position switch.

Upon completing a 360° turn from its initial starting position (the "twelve o'clock" position), the control valve that permits the held media to enter the second cylindrical chamber, and the control valve that permits the flow of media from the spent media transfer chamber to the third cylindrical chamber are opened by a solenoid activated by a sensor included in a regulator assembly.

A sensor can be selected such that any parameter associated with cell or tissue culture or the formation of a desired product can be measured. In one embodiment, the sensor measures a change in pH.

In another embodiment, the sensor measures the change in ammonia ion concentration.

In yet another embodiment, the regulator includes both a sensor that measures a change in pH and a sensor that measures the change in ammonia ion concentration.

The regulator assembly also includes first and second solenoids that are operatively connected to magnets. The gravity sensitive position switch activates the first solenoid which actuates a magnetic field between the magnet connected operatively thereto and an opposing magnet located inside the spent media transfer chamber. The magnetic field formed by the first solenoid with the opposing magnet opens the control valve that permits media to flow from the second cylindrical chamber into the spent media chamber.

The second solenoid is activated when the sensor detects a change in media conditions in the second cylindrical chamber and sends an electrical signal to the second solenoid. The second solenoid actuates a magnetic field between magnets connected thereto and opposing magnets situated inside the spent media transfer chamber and the fresh media transfer chamber, thereby opening valves that permit the flow of media from the fresh media transfer chamber to the second cylindrical chamber and the flow of media from the spent media transfer chamber to the third cylindrical chamber.

The invention also provides a method of culturing cells using the ARBS wherein growth media is introduced into the first cylindrical chamber and cells or tissue are separately introduced into the second cylindrical chamber. The cells or tissue are cultured by rotating the ARBS in a clockwise or counterclockwise-manner.

In this method new growth media automatically flows from the first cylindrical chamber to the second cylindrical chamber and the pH or cellular product concentration in the second cylindrical chamber can be monitored. When a desired pH or cellular product concentration value is measured by the sensor, the sensor actuates the solenoids which open the control valves causing spent media to flow from the second cylindrical chamber to the third cylindrical chamber and new growth media to flow from the first cylindrical chamber into the second cylindrical chamber.

The method can also include a recovery step where cellular products are recovered from the second or third chamber of ARBS system.

Cellular products include whole cells, tissue, cellular parts, secreted molecules or products of cellular metabolism.

DESCRIPTION OF THE INVENTION

Figure 1:
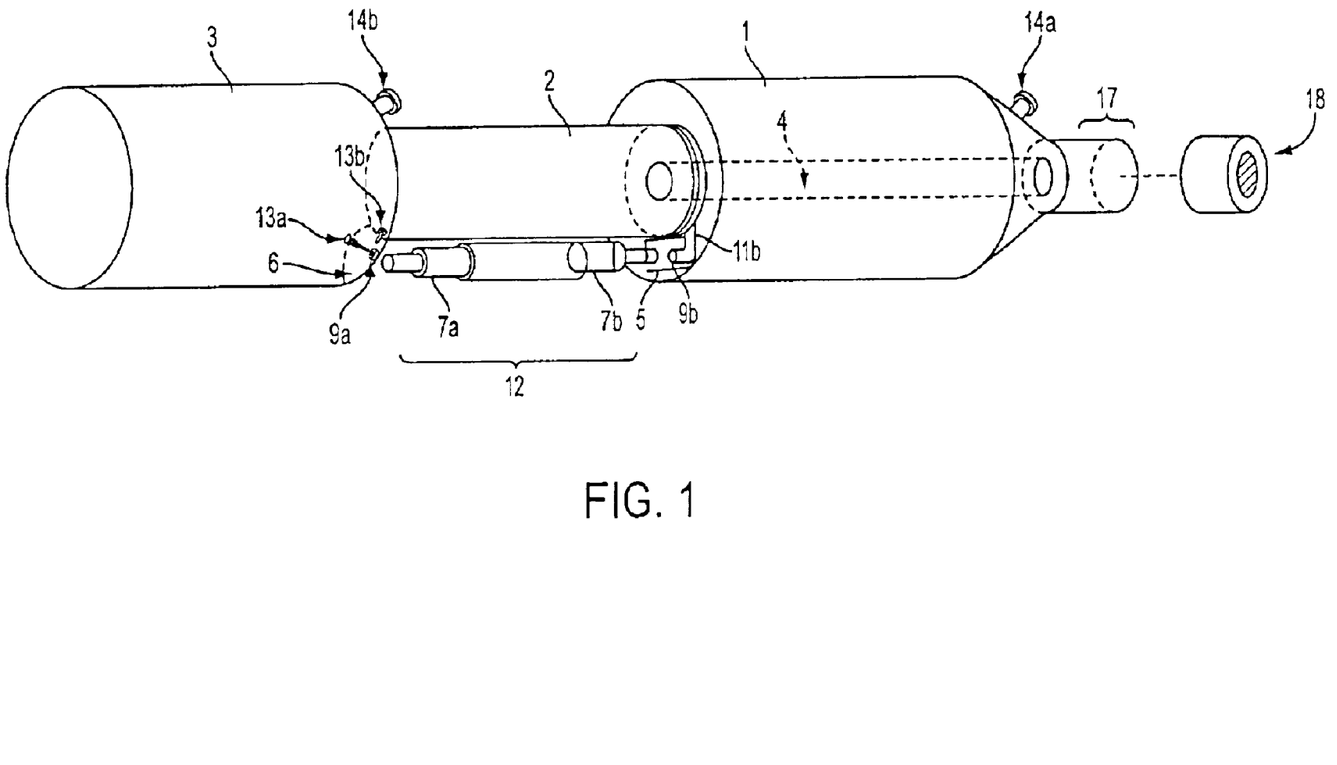
FIG. 1 shows the ARBS of the invention as assembled. The components of the assembled system shown in this Figure are exemplary of an electromechanical embodiment of the invention.

The ARBS of the invention as depicted in FIG. 1 can be generally characterized by three compartments: fresh media reservoir (1), growth chamber (2), and spent media reservoir (3). Constant media flow is achieved automatically between fresh media and spent media reservoirs (1) and (3), respectively, and the growth chamber (2) with the aid of spring loaded valves which open and close while the ARBS rotates 360° about its longitudinal axis. The opening and closing of these valves can be controlled either electromechanically or physiochemically.

Figure 2:
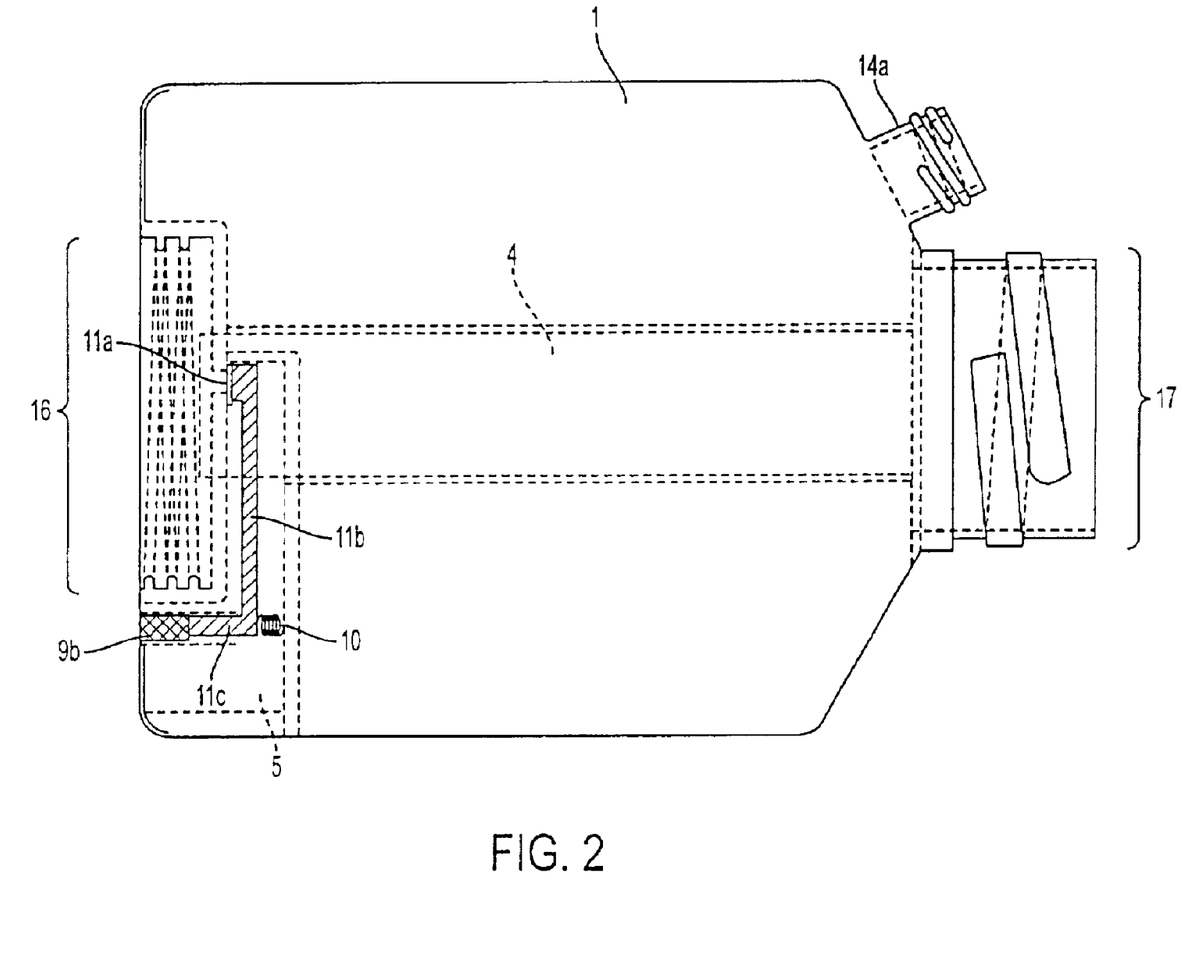
FIG. 2 shows an expanded view of the upper portion of the ARBS.
Figure 3:
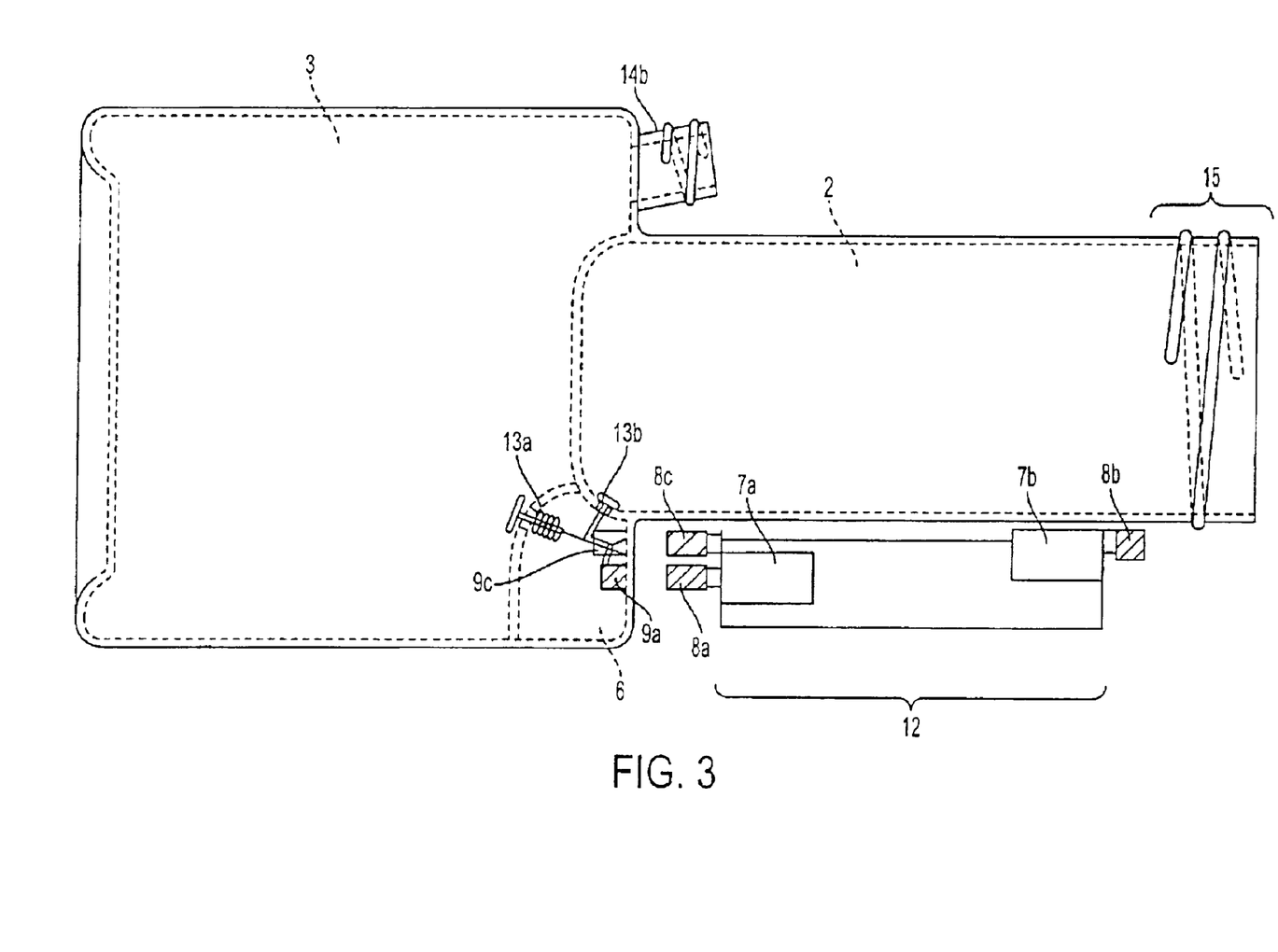
FIG. 3 shows an expanded view of the lower portion of the ARBS. The components of the system shown in this Figure are exemplary of an electromechanical embodiment of the invention.

The ARBS is also characterized by having a bipartite assembly as depicted in FIGS. 2 and 3 wherein a spirally-threaded member (15) screws into a spiral-thread receiving member (16). Similarly, spirally-threaded member (15) can be unscrewed from spiral-thread receiving member (16) disassembling the ARBS and exposing growth chamber (2). The skilled artisan exercising routine skill will be able to incorporate alternate assembly and disassembly means including but not limited to clasps, clips, male/female protrusion type attachment, vacuum seals, or other means of fastening one member to another.

Growth chamber (2) is the main culturing compartment into which cells or tissue are implanted; into which fresh culture media is introduced from fresh media reservoir (1); and from which spent media is expelled into spent media reservoir (3).

Culture Media

Various cell culture media types are useful in conjunction with the ARBS and are readily available through online and catalogue distributors (e.g., GIBCO, Sigma, and CellTech, Inc.) and can be purchased in a range of volumes having a variety of nutrient combinations; with or without supplements (e.g., amino acids, vitamins, electrolytes); or with or without additives such as antibiotics and/or antioxidants. It is within routine skill in the art to determine which media type is best suited for a specific cell culture protocol based on the cell or tissue types to be cultured.

For example, Dulbecco's Modified Eagle Medium (DMEM) is a commonly used culture media which can be obtained in a variety of forms including a high glucose preparation, a low glucose preparation, and an F-12 preparation containing L-glutamine and pyridoxine hydrochloride. DMEM is ideal for supporting and maintaining a range of mammalian cell types. DMEM was originally developed for the growth of mouse embryo cells as a modification of Basal Medium Eagle (BME) media but with four times the amino acid and vitamin concentration. The low glucose formulations, 1.0 g/L, are recommended for the maintenance of high density cultures and the growth of cells in agar. The high glucose formulations, 4.5 g/L, are widely used for anchorage-dependent cell types (e.g., Chinese hamster ovary cells or human embryonic kidney cells) (Dulbecco, R et al., (1959) *Virology* 8: 396–397, and Smith, J D et al., (1960) *Virology* 12: 185, see also Moton, H J (1970) *In Vitro* 6: 89).

Also useful in culturing cells or tissue with the ARBS are the following media types which are provided herein by way of example and not for the purposes of limitation:

TABLE 1

Cell Culture Media

| MEDIA | REFERENCE |
|---|---|
| Alpha Minimum Essential Medium | Eagle, H. (1959) Science 130: 432–437. |
| BME-Cyroprotective Media | Eagle, H. (1955) Proc. Soc. Exp. Biol. Med., 89: 362–364. |
| Ham's Media | Ham, RG, et al., (1965) Proc. Natl. Acad. Sci. USA 53: 288–293; Ham, RG, et al., (1963) Exp. Cell Res. 29: 515–526. |
| Iscove's Modification of Dulbecco's Medium | Iscove, NN, et al., (1978) J. of Exptl. Med. 147: 923–933. |
| Leibovitz's | Leibovitz, A. (1963) Am. J. Hyg. 78: 173–180. |
| McCoy's | McCoy, TA, et al., (1959) Proc. Soc. Exptl. Biol. Med. 100: 115–118. |
| Medium 199 | Morgan, JF, et al., (1950) Proc. Soc. Exptl. Biol. Med. 73: 1–8. |
| Minimum Essential Medium | Eagle in Science, supra. |
| NCTC | McQuilkin, WT, (1957) J. Nat. Canc. Inst. 19: 885–907. |
| RPMI | Moore, GE, et al., (1967) J. Am. Med. Assoc. 199: 87–92. |
| GMEM | Eagle in Science, supra. |

In devices designed for high-density cell culture, (e.g., miniPERM™, spinner flasks, roller bottles, or fermenters) cells and tissue are subjected to considerable shear forces. Shear forces can be controlled either by regulating the speed at which the bioreactor, i.e., a roller bottle, revolves or by the addition of anti-shear supplements into the culture media. One such supplement is cellPROTECT™ available from VivaScience, AG. The cellPROTECT™ supplement increases the viscosity of the medium and protects cells from shear force/stress experienced in culture. The cellPROTECT™ supplement is added to the culture medium to a concentration of about 0.05% to about 0.1% of the final volume. Viscosity increasing supplements like cellPROTECT™ or media types having high viscosities may be used in the present invention so long as they are compatible with the ARBS and their of viscosity does not impede the flow of media through the valves and between the chambers and reservoirs.

ARBS Electromechanical Assembly

In one embodiment of the ARBS shown in FIGS. 1 and 3, constant media replenishment and disposal is achieved by the flow of media between the compartments through replenishment valve (11a), disposal valve (13a), and waste transfer valve (13b). In this embodiment, the valves are controlled electromechanically by a detachable regulator (12) having a pH or ammonia ion sensor or a sensor capable of detecting both pH shifts and changes in ammonia ion concentration. The Regulator (12) further includes upper solenoid (7b), lower solenoid (7a), position sensor and regulator magnets (8a), (8b), and (8c) operatively connected to solenoids (7a) and (7b) as shown in FIG. 3.

pH sensors

In one embodiment of the ARBS, regulator (12) can include a pH sensor or meter which activates upper solenoid (7b) and lower solenoid (7a) as shown in FIGS. 1 and 3. If, for example, regulator (12) includes a pH sensor or meter, a disposable pH probe (not shown) can be situated internally in growth chamber (2) that is operatively connected to regulator (12) through an aperture (not shown) on the surface wall of growth chamber (2) (see FIG. 3). The disposable pH probe is detachable from regulator (12) such that regulator (12) can be reused while the remainder of the ARBS assembly is disposable.

Devices for measuring pH in a liquid are well known. Glass sensors having membrane type electrodes are commonly and reliably used as standards for pH measurements (see e.g., Ohkawa H, *Tanpakushitsu Kakusan Koso* [Japanese] (1998) 43(3): 272–80; and Moore E W, *Gastroenterology* (1968) 54(4): 501-7). Non-glass pH sensors are also useful as components of regulator (12) and are typically prepared using solvent polymeric membranes (described by Pretsch et al., (1986) *Anal. Chem.* 58: 2285–2289, hereby incorporated by reference). Within the category of non-glass sensors are those having planar configurations that are typically smaller than glass sensors and much less expensive to manufacture as well as operate. Examples of planar sensors can be found in U.S. Pat. Nos. 5,554,272 to Benco, and 5,702,575 to Foos which are hereby incorporated by reference in their entirety. Instruments containing planar sensors are available commercially. The planar format of the sensors typically comprise relatively thin layers of material applied to a substrate bases using thick-film or thin-film techniques, including, for example, silk-screen printing. Material used as substrates can be $Al_2O_3$ or $Ta_2O_5$ deposited by means of PLD (pulsed laser deposition) process or $Si_3N_4$ applied by PECVD (plasma-enhanced chemical vapor deposition) and LPCVD (low pressure chemical vapor deposition) on silicon field-effect structures. Both sensor types exhibit a high pH sensitivity and long-term stability in operation. In addition, polyaniline film is useful as a high sensitivity planar pH indicator (Takenaka, Y et al., (1990) *Chemical Sensors* 6 (*Supplement A*): 77–80, and Takenaka Y et al., at 81–84, and Shinohara, H et al., *Chemical Sensors* 6 (*Supplement A*):85–88).

If, for example, DMEM is the media selected for cell or tissue culture, the typical pH optimum will be about 7.4 to about 7.5. The pH sensor of regulator (12) is preferably calibrated to respond to pH changes below about 7.4, preferably below about 7.2, more preferably below about 7.0, and most preferably below about 6.8.

The ARBS can also support cell cultures of explants (primary cells) taken directly from a living organism (e.g., biopsy material or aspirations), preferably a mammal, and more preferably a human. These cell cultures consist of mixed cell type populations. The optimal pH for culture of primary cells is about 7.0 and a pH sensor included in regulator (12) is preferably calibrated to detect pH shifts below about 7.0; preferably below about 6.9; and most preferably below about 6.8, for primary cell culturing.

It is within routine skill in the art to calibrate a pH meter and determine the optimal pH ranges tolerated by specific cell culture protocols or cell or tissue types used, and thus the regulator (12) is not limited in application to any one cell culture protocol or cell or tissue type.

Ammonia Ion Sensors

Regulator (12) can also include an ammonia ($NH_3$) ion sensor for analyzing growth conditions in growth chamber (2). Ammonia ion sensors can include polymer membrane electrodes consisting of various ion- exchange materials in an inert matrix such as porous Teflon™, polyvinylchloride (PVC), polyethylene or silicone rubber. After the membrane is formed, it is sealed to the end of a PVC tube. Electrodes of this type include potassium, calcium and nitrate.

Ammonia ion sensors having solid state electrodes utilize relatively insoluble inorganic salts in a membrane. Solid state electrodes exist in homogeneous or heterogeneous forms. In both types, potentials are developed at the membrane surface due to the ion-exchange process. Examples of solid state electrodes include silver/sulfide, chloride and fluoride.

Ammonia ion sensors having gas sensing electrodes are available for the measurement of ammonia, carbon dioxide, nitrogen oxide and sulfur dioxide. These electrodes have a gas permeable membrane and an internal buffer solution. The pH of the buffer solution changes is response to gas. The change is detected by a combination pH sensor within the housing. Due to the construction, gas-sensing electrodes do not require an external reference electrode.

In this embodiment, cells or tissue to be cultured are implanted into growth chamber (2). Cells and tissue can be implanted directly into growth chamber (2), the inner surfaces of which may be optionally derivatized, or can be introduced via a scaffold seeded with the cells or tissue. To facilitate cell or tissue implantation into growth chamber (2), the ARBS is preferably separated (unscrewed) at the interface of spirally-threaded member (15) and spiral-thread receiving member (16).

Derivatized Inner Surface of Growth Chamber

The inner surface of growth chamber (2) can be optionally derivatized to facilitate cell attachment by methods known in the art. The inner surface of the growth chamber can be derivatized with amino, active halo, hydroxy, or thiol groups, or a substituted N-hydroxymethyl acetamide where the substituent is an active halogen or pseudohalogen. Proteins or linear peptides can be bound by contacting the proteins or linear peptides in an aqueous medium with a functionalized surface having active halogen, activated carboxy groups, e.g., esters, or the like, under mild conditions for sufficient time to complete a derivatization reaction. Any remaining unreacted functional groups may be blocked by using an appropriate small molecule-blocking agent. For example, active halogens may be blocked with aliphatic amines, thiols with maleimide, or the like. In some embodiments, there may be no need to block excess reactive groups, since they will not interfere with the subsequent steps in the derivatization process.

If immunological cells, e.g., B-cells are selected for culture, the inner surface of growth chamber (2) can be derivatized with a B-cell recognized antigen (e.g., CD20) or by specific binding to soluble antigen wherein such antigen may be added to the cells so that those cells having surface immunoglobulins which recognizes the antigen will bind the antigen to form a complex which is endocytosed and processed. A fragment of the antigen with the cell's MHC antigen will be presented. By adding T-cells to the medium which are restricted by the B-cells, T-cells which recognize the antigen fragment will secrete lymphokines, resulting in proliferation of the B-cells.

Cell Culturing Using an Electromechanical Embodiment of the ARBS

Upon implantation the ARBS is placed into a rolling apparatus where it revolves around its longitudinal axis. A gravity sensitive position switch (not shown) detects that the ARBS has turned 180° relative to its starting position (hereafter referred to as the "6o'clock" position). This gravity sensitive position switch can be, for example, a mercury tilt switch or weighted lever switch.

Mercury tilt (or "tip-over") switches are based on simple construction having no moving parts other than shifting mercury. Mechanically, these switches experience little wear and have long life expectancies with the average number of operations in the tens of millions (Durakool, DANA, distributed by American Electronic components).

Non-mercury based "tip-over switches" can also be used as rotation sensors. One such non-mercury switch can be obtained from Comus, and has a 0.360"×0.310" housing and is suitable for operation in a temperature range from −37 to 100° Celsius (also available from DuraKool, DANA).

At the 6o'clock position, if regulator (12) detects a shift in pH or change in ammonia ion concentration, or both, in the media of growth chamber (2) that exceeds a predetermined threshold, regulator (12) sends an electrical signal activating lower solenoid (7a). Activated lower solenoid (7a) engages regulator magnet (8a) forming a magnetic field with opposing inner magnet (9a). Inner magnet (9a) in turn causes constriction of a spring in waste transfer valve (13b) thus opening the valve. Opened waste transfer valve (13b) allows media to flow from growth chamber (2) into waste transfer chamber (6).

Waste transfer chamber (6) has the capacity to hold all of the media volume in growth chamber (2), typically about 15 mL. At the 6o'clock position, waste transfer chamber (6) can be filled to entirety if so desired but is preferably filled to about 6% capacity, more preferably to about 7% capacity, and most preferably to about 8% capacity. The length of time needed for spent or fresh media transfer from one chamber to the next relates in part to the size of the hole between the chambers. The solenoid would be open through the whole 30 degrees of the "6 and 12o'clock" positions. The amount of time that the position would be open would depend on the speed of rotation of the device.

When the ARBS completes one revolution (360° from its starting position; referred to as the "12o'clock" position, hereafter) fresh media transfer chamber (5) scoops about 8 mL, preferably about 9 mL, and most preferably about 10 mL of fresh media from fresh media reservoir (1).

At the 12o'clock position upper solenoid (7b) is activated by electrical signals from regulator (12) and engages regulator magnets (8b) and (8c). Regulator magnet (8c) forms a magnetic field with opposing inner magnet (9c) forcing disposal valve (13a) to open and deposit the spent media that entered waste transfer chamber (6) at the 6o'clock position into spent media reservoir (3). Concurrently, upper solenoid (7b) also activates regulator magnet (8b) forming a magnetic field with opposing inner magnet (9b). Inner magnet (9b) depresses spring (10) by way of plunger member (11c) pushing arm (11b) along the ARBS' horizontal axis thus opening replenishment valve (11a). Opened replenishment valve (11a) allows the scooped media from fresh media transfer chamber (5) to enter growth chamber (2).

Cell and tissue cultures require aeration for proper growth. As the ARBS revolves, growth chamber (2) is aerated by aeration tube (4) connecting growth chamber (2) with ambient air which is preferably sterile. As shown in FIGS. 1 and 2, aeration tube (4) extends through fresh media reservoir (1) and protrudes through screw-top (17) where it is exposed to ambient air through vented cap (18).

The ARBS preferably completes one revolution to equilibrate before regulator (12) takes another reading.

Additional components of the ARBS assembly include tube cap (14a), permitting the replacement of fresh media in fresh media reservoir (1) or addition of additives, nutrients, growth factors and the like without disassembling the system and tube cap (14b), permitting the removal of spent media from spent media reservoir (3) without disassembling the system. Both tube caps (14a) and (14b) can be capped with appropriate screw tops (not shown) during ARBS use.

The media removed from spent media reservoir (3) through tube cap (14b) can be either discarded or saved. In some methods of cell culturing using the ARBS, spent media is saved to exploit desired cellular products secreted during cell growth and metabolism. As used herein the term "cellular products" is meant to encompass whole cells or tissue or any sub-structure therein (e.g., cell organelles or membranes), secreted ions, secreted compounds, secreted molecules, antibodies or other immunoglobulins, antigens, proteins, cytokines, hormones, organic compounds, pharmaceutical compounds, or other biomolecules of interest. Cellular products also include those substances (e.g., ions) detected by a sensor included in regulator (12), the detection of which actuates the flow of media between the chambers of the ARBS. These cellular products can be harvested from the spent media collected from spent media reservoir (3).

The inner surface of growth chamber (2) may be derivatized to facilitate cell attachment. Additionally, particles or a scaffold may also be used for cell or tissue attachment. These particles, e.g., beads, or scaffold may be derivatized. The preferred shape of the scaffold is that of a cylindrical block-like member that can be readily inserted into and removed from growth chamber (2). Other shapes that can be readily inserted into and removed from growth chamber (2) are also contemplated within the scope of the invention, for example, a disk shaped scaffold. The open pore foam of the scaffold is particularly desirable in that the structure allows for easy rinsing and detachment of cells using various known cell recovery techniques and materials.

One suitable mechanism for rinsing and detaching cells from the scaffold uses a solution containing a proteolytic enzyme, such as trypsin. Other suitable mechanisms for detaching cells include sonication or agitation so long as the force applied to the cells does not induce lysis. However, if the cells are ultimately used in extraction assays (e.g., to isolate intracellular cell products, metabolites, or cell membrane surface molecules or moieties) prevention of lysis is less important. The skilled artisan will appreciate that any method known in the art is useful in rinsing or detaching the cultured cells from the scaffold as befits the ultimate use of the cultured cells.

ARBS Physiochemical Assembly

In another embodiment, the ARBS can be assembled by substituting a pH hydrogel for regulator (12), which makes the entire ARBS disposable.

In the physiochemical embodiment of the ARBS, pH hydrogel dilation and contraction in response to pH shifts exerts a force on replenishment valve (11a), disposal valve (13a), and waste transfer valve (13b) causing them to open and close.

The pH hydrogels used herein are polymeric materials which swell in water and other solvents, absorbing the fluid within the polymer network without dissolving. Hydrophilic hydrogels have large water contents at equilibrium and good biocompatibility. pH-sensitive hydrogels have been the most widely studied of the hydrophilic hydrogels. The pH-sensitive hydrogels are cross-linked to form a stabilized gel with several types of crosslinking forces such as covalent bonds, hydrogen bonds, or hydrophobic interactions. Acidic hydrogels by definition will be ionized and hence swollen at high pH, and uncharged and un-swollen at low pH. Swelling behavior of a basic hydrogel has the opposite dependence on pH which makes it suited for application in the ARBS. The pH sensitivity is caused by pendant acidic and basic groups such as carboxylic acid, sulfonic acid, primary amine, and quaternary ammonium salts. Carboxylic acid groups for example are charged at high pH and uncharged at low pH, whereas the reverse is true for primary amine groups and quaternary ammonium salts. The transition pH for a given pendant group is determined by the pKa value for that pendant group. Hence by selecting pendant groups with the appropriate pKa values, a hydrophilic hydrogel can be constructed which can be ionized reversibly in response to any level of pH stimuli leading to changes in properties of a gel. {the pH range would depend on the particular cell type selected or cellular product desired . The hydrogel is chosen for the target pH range desired, preferably with a rapid swelling/de-swelling transition occurring within the targeted pH range. The position of the hydrogel and valves would be critical and an external magnet that would need to be attached to the roller rack would be needed to act as the position sensor.

The preferred pH-sensitive hydrogels are derived from a number of polymeric compounds such as: poly(aklyl acrylate), poly(acrylmethacrylate), poly(2-hydroxyethyl methacrylate) (HEMA), poly(2-hydroxypropylmethacrylate) (HPMA), poly(acrylamide), poly(N-vinyl pyrrolidone), poly(vinyl alcohol) (PVA), poly-ethylene oxide (PEO), poly(etherurethane), and polyelectro-lyte. The monomers used to synthesize the homopolymers just listed can also be used in various combinations to form copolymers. pH-sensitive hydrogels formed from these polymers reversibly contract and dilate upon addition of acid and alkaline, alternately. It has been shown that the response to a pH change can be fast and reversible after abrupt changes in pH for poly(methyl methacrylate-co-N,N-dimethylaminoethyl methacrylate) hydrogels. Persons having ordinary skill in the art will know how to combine several polymers to form composite pH sensitive hydrogels.

The equilibrium degrees of swelling and the conformation changes of pH-sensitive hydrogels are influenced by several factors such as the charge of the ionic monomer, pKa of the ionizable group, concentrations of ionizable pendant group in the network, pH, ionic strength, the dielectric constant of the medium, crosslinking density, hydrophilicity and hydrophobicity of polymer backbone. These factors are discussed in Helle B, et al., *pH-Sensitive Hydrogel; Characteristics and Potential in Drug Delivery in Properties, Preparation, and Application* (Eds. Harland et al.) 1992.

The charge of the ionic monomer influences the conformational changes of pH-sensitive hydrogels. An acidic hydrogel will be uncharged at low pHs, but will ionize at high pHs. Thus, the equilibrium degree of swelling will increase when pH is enhanced in a hydrogel containing acidic pendant groups. Swelling of a hydrogel has the opposite dependence on pH. Hydrogels based on methacrylic acid, sulfoxyethyl methacrylate, HEMA, or HPMA have been generally used to obtain acid, basic, and ampholytic gels. Swelling as a function of the type of ionic group has been studied (Chen, L L et al., (1998) *Pharm. Dev. Technol* 3(2): 241–9).

The pKa value of pendant ionizable groups in the gel influences the pH-swelling curve (Chen, supra). A decrease in the pKa value of a basic ionizable group shifts the curve toward lower pH. It has been demonstrated that the swelling response is most sensitive to pH at a pH value close to the pKa value of the ionizable group of the hydrogel (Eichenbaum G M, et al., (1998) *Macromolecules* 31(15): 5084–93). The concentration of ionizable monomers in the hydrogel is significant to the swelling and pH-sensitivity of the gel. This effect depends on the relative hydrophilicity of the ionizable monomer compared to the neutral co-monomer. The hydrophobicity and hydrophilicity of the backbone of the pH-sensitive polymer affects swelling. It has been shown that increasing hydrophobicity of the polymer backbone decreases the pH-sensitivity of the copolymer poly(n-alkyl methacrylate-co-N,N-dimethylaminoethyl methacrylate) and copolymer styrene and 4-vinyl pyridine (VP). Buffer composition and ionic strength affect the swelling of the pH-sensitive hydrogels. Counterions shield charges on the polymeric backbones. The concentration of ions inside and outside of the gel will be equal as well as osmotic pressure inside the gel will decrease when the concentration of ions outside the gel increases. A buffer containing multivalent ions is able to neutralize several charges inside the gel. Cross-linking density is important for pH-sensitive swelling. An increased cross-linking density will restrict the equilibrium degree of swelling. This effect is more pronounced if the gel is ionized by a pH change. The network properties of the hydrogels are mainly influenced by the synthesis variables, particularly chemical composition and cross-linking density (Chen, supra, see also Mandal T K et al., (2000) *Pharm. Dev. Technol.* 5(4): 555–60).

The preferred pH-sensitive hydrogel valves include copolymers synthesized from various types of methacrylate derived monomers by free radical solution polymerization. These copolymers are tough, flexible polymers rather than soft gels; they are highly biocompatible; and they are inert and nondegradable and as such ideal for roller bottles such as the ARBS which is constantly exposed to shear stress from the movement of media between compartments. For example, the swelling of gels which are copolymers of N,N-diethyl-aminoethyl methacrylate (DEAMA) and 2-hydroxypropylmethylacrylate (HPMA) increases with decreasing pH of the medium. This has been shown by Ishihara K., et al., (1984) *Poly J.* 16: 625–631. By contrast, water content of a HEMA homopolymer is independent of the pH of the medium. Thus, changes in water content with the pH of the HPMA copolymer hydrogel result from the introduction of the DEAMA moiety. The DEAMA moiety is considered to be protonated when the pH of the medium decreases, which increases the hydrophilicity of the DEAMA moiety and the hydrogel. The water content of DEAMA and HPMA copolymer hydrogels are reversible with respect to pH changes.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice in the art to which the invention pertains and as may be applied to the essential features.

What is claimed is:

1. A multi-chambered roller bottle system having at least three cylindrical chambers comprising,
    a first cylindrical chamber suitable for use as a cell growth media reservoir having at least four ports where two ports are located at an outside wall, one providing access to an air source and the other providing general access to the first cylindrical chamber, and where the other two ports are located at an inside wall where the first and second cylindrical chambers abut, one port provides access to an air source for the second cylindrical chamber via a duct connecting to the port on the outside wall providing air access and the other port provides controlled fluid communication with the second cylindrical chamber via a control valve;
    a second cylindrical chamber suitable for cell or tissue growth having at least three ports, two located at the side wall that abuts with the first cylindrical chamber, one port being coextensive with the port providing air access located at the inside side wall of the first cylindrical chamber and the other port aligned with the port of the first cylindrical chamber providing controlled fluid communication, and the third port providing controlled fluid communication with a third cylindrical chamber via a control valve;
    a third cylindrical chamber suitable for receiving spent media and having at least two ports, one located on an outside wall that abuts with the second cylindrical chamber and provides general access to the third cylindrical chamber and the second port aligned with the third port of the second cylindrical chamber providing controlled fluid communication with the second cylindrical chamber; and
    a control means for sequentially actuating the valves to produce a controlled fluid flow from each of the respective chambers to the other at predetermined positions of rotation of the chambers;
    wherein the first, second and third cylindrical chambers are interconnected so as to permit rotation of the cylindrical chambers as a single assembly about a rotational axis and wherein the control of fluid communication permits growth media from the first cylindrical chamber to be introduced to the second cylindrical chamber and spent media from the second cylindrical chamber to be removed from the second cylindrical chamber to the third cylindrical chamber.

2. The roller bottle system of claim 1 wherein the port providing the first cylindrical chamber controlled fluid communication with the second cylindrical chamber includes a valve controlling fluid flow through the port and a fresh media transfer chamber located in the first cylindrical chamber wherein two of the walls of the fresh media transfer chamber are portions of the curved wall of the first cylindrical chamber and the inside wall and which fresh media transfer chamber scoops up and holds growth media from the first cylindrical chamber during rotation of the roller bottle from a six o'clock position to a twelve o'clock position, wherein the valve is closed in the six o'clock position and actuated in the twelve o'clock position to release media into the second cylindrical chamber.

3. The roller bottle system of claim 1 wherein the port providing controlled fluid communication with the third cylindrical chamber includes a first valve controlling fluid flow through the port to the third cylindrical chamber and a spent media transfer chamber located in the third cylindrical chamber which receives spent media from the second cylindrical chamber when a second valve is actuated in response to a sensor present in the second cylindrical chamber wherein two of the walls of the spent media transfer chamber are portions of the curved wall of the third cylindrical chamber and the inside wall and which chamber during rotation of the roller bottle from a six o'clock position to a twelve o'clock position, wherein the first valve is closed and the second valve actuated in the six o'clock position, the actuated second valve permits spent media to flow into the spent media transfer chamber and the first valve is actuated in the twelve o'clock position to release media into the third cylindrical chamber.

4. The roller bottle system of claim 1 wherein the first and second cylindrical chambers are interconnected by conjoining a male attachment member with a female attachment member, wherein each of the members surround the port and duct providing air access to the second cylindrical chamber.

5. The roller bottle system of claim 1 wherein the control means comprises gravity sensor switch, a first and a second solenoid wherein the first solenoid is operatively connected to a first and a second magnet, the second solenoid is operatively connected to a third magnet.

6. The roller bottle system of claim 1 further comprising at least three magnets; at least two magnets situated at the inner wall of the third cylindrical chamber that abuts the second cylindrical chamber; and at least one magnet situated at the inner wall of the first cylindrical chamber that abuts the second cylindrical chamber, the at least three magnets situated as opposing magnets to the magnets operatively connected to the first and second solenoids.

7. The roller bottle system of claim 1 wherein one or both of the first and second solenoids are activated and wherein one or more operatively connected magnets form a magnetic field with one or more opposing magnets, one or more opposing magnets opening one or more control valves.

8. The roller bottle system of claim 7 wherein the first solenoid is activated by a sensor.

9. The roller bottle system of claim 8 wherein the sensor monitors changes in pH.

10. The roller bottle system of claim 8 wherein the sensor monitors changes in the concentration of a cellular product.

11. The roller bottle system of claim 10 wherein said cellular product is ammonia ion.

12. The roller bottle system of claim 7 wherein the second solenoid is activated by a gravity sensitive position switch.

13. The roller bottle system of claim 12 wherein the gravity sensitive position switch is selected from a mercury tilt switch or a weighted lever switch.

14. The roller bottle system of claim 7 wherein the activated second solenoid opens the control valve that actuates the transfer of growth media from the second cylindrical chamber to the spent media transfer chamber.

15. The roller bottle system of claim 1 wherein the control means is positioned on the outside of the second chamber so that the control valves can be directly actuated in a position dependent manner.

16. The roller bottle system of claim 1 wherein the valve comprises a physiochemical responsive hydrogel.

17. A method for cell and tissue culture comprising the steps of:
    A) introducing growth media into the first cylindrical chamber and cells or tissue into the second cylindrical chamber of the roller bottle system of claim 1, B) culturing the cells or tissue by rotating the roller bottle about its longitudinal axis, C) causing new growth media to flow from the first cylindrical chamber to the second cylindrical chamber, D) monitoring a cell or tissue culture parameter in the second cylindrical chamber and causing spent media to flow from the second cylindrical chamber to the third cylindrical chamber when a predetermined threshold cell or tissue culture parameter value is measured.

18. The method according to claim 17 wherein step C) involves introducing growth media from the first cylindrical chamber through an opening into a first transfer chamber during rotation wherein the fresh media transfer chamber comprises walls and the port providing controlled fluid communication with the second cylindrical chamber and wherein the valve is closed when the roller bottle is in a six o'clock position causing the fresh media transfer chamber to hold and retain media and actuated in a twelve o'clock position to release the retained media into the second cylindrical chamber.

19. The method according to claim 17 wherein step D) involves introducing spent media from the second cylindrical chamber, containing a threshold signal sensor, through a opening controlled by a first valve in response to the sensor signal into a spent media transfer chamber during rotation of the roller bottle wherein the spent media transfer chamber comprises walls, a second valve controlling the port providing controlled fluid communication with the third cylindrical chamber and the port and wherein the second valve is closed when the roller bottle is in a six o'clock position causing the second transfer chamber to hold and retain media, the first valve, only actuated to an open position in the six o'clock position when a cell or tissue culture parameter value threshold is met, allowing the spent media transfer chamber to fill with spent media, and the second valve opens in a twelve o'clock position to release the spent media into the third cylindrical chamber.

20. The method of claim 17 wherein the cells or tissue attach to a surface.

21. The method of claim 17 wherein the cells or tissue attach to a derivatized surface.

22. The method of claim 17 wherein the cells or tissue attach to a removable surface.

23. The method of claim 17 wherein the cells or tissue attach to a removable derivatized surface.

24. The method of claim 17 further comprising the step:

E) recovering cellular products from the roller bottle system.

25. The method of claim 24 wherein the recovering step includes the removal of cellular products from the second and/or third cylindrical chamber.

26. The method of claim 17 wherein the cell or tissue culture parameter is pH or ammonium ion concentration.

* * * * *